(12) United States Patent
Navis

(10) Patent No.: US 8,435,226 B2
(45) Date of Patent: May 7, 2013

(54) CATHETER

(75) Inventor: John A. Navis, Oswego, IL (US)

(73) Assignee: Merit Medical Systems, Inc., South Jordan, UT (US)

(*) Notice: Subject to any disclaimer, the term of this patent is extended or adjusted under 35 U.S.C. 154(b) by 920 days.

(21) Appl. No.: 12/316,434

(22) Filed: Dec. 12, 2008

(65) Prior Publication Data

US 2010/0152705 A1   Jun. 17, 2010

(51) Int. Cl.
*A61M 25/00* (2006.01)

(52) U.S. Cl.
USPC .......................... 604/523; 604/529; 604/533

(58) Field of Classification Search .................. 604/523, 604/529–530, 533–535
See application file for complete search history.

(56) References Cited

U.S. PATENT DOCUMENTS

| 6,402,736 | B1 * | 6/2002 | Brown et al. .................. 604/523 |
| 7,766,049 | B2 * | 8/2010 | Miller et al. .................. 138/116 |

* cited by examiner

*Primary Examiner* — Kevin C Sirmons
*Assistant Examiner* — Deanna K Hall
(74) *Attorney, Agent, or Firm* — Stoel Rives LLP

(57) ABSTRACT

A drainage or infusion catheter comprises a flexible tube that terminates at the distal portion thereof in an apertured spiroid. The flexible tube has one or more subcutaneous cuffs, affixed at the midportion of the tube, and one or more pairs of opposed offsets of the tube between the proximal end and the distal portion thereof.

19 Claims, 2 Drawing Sheets

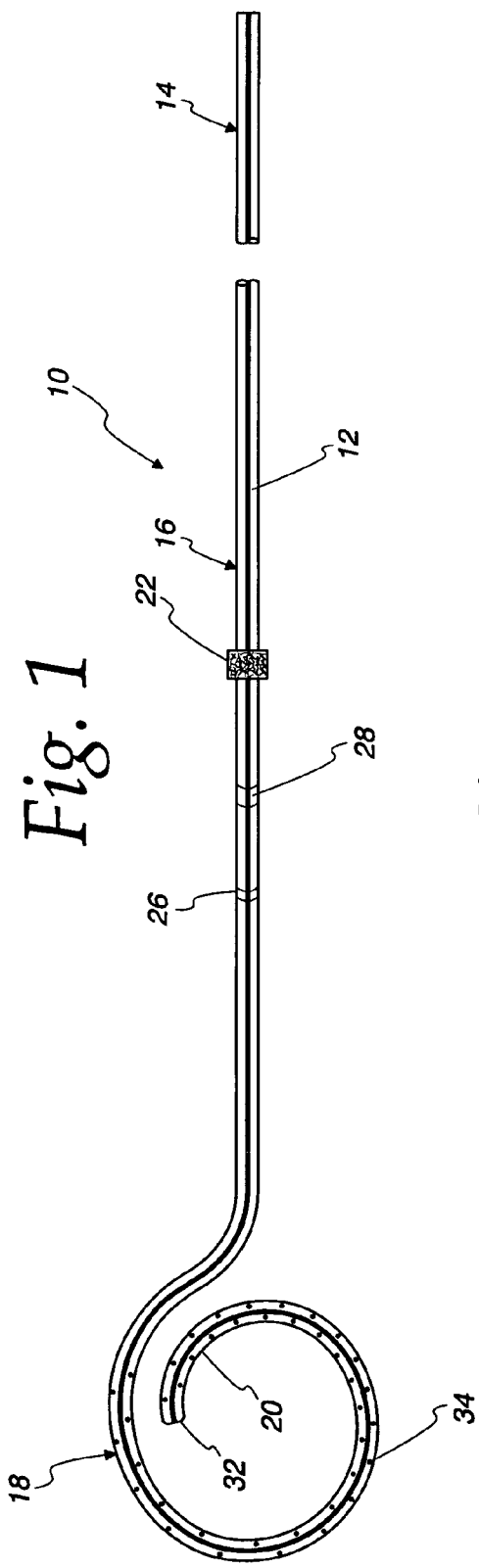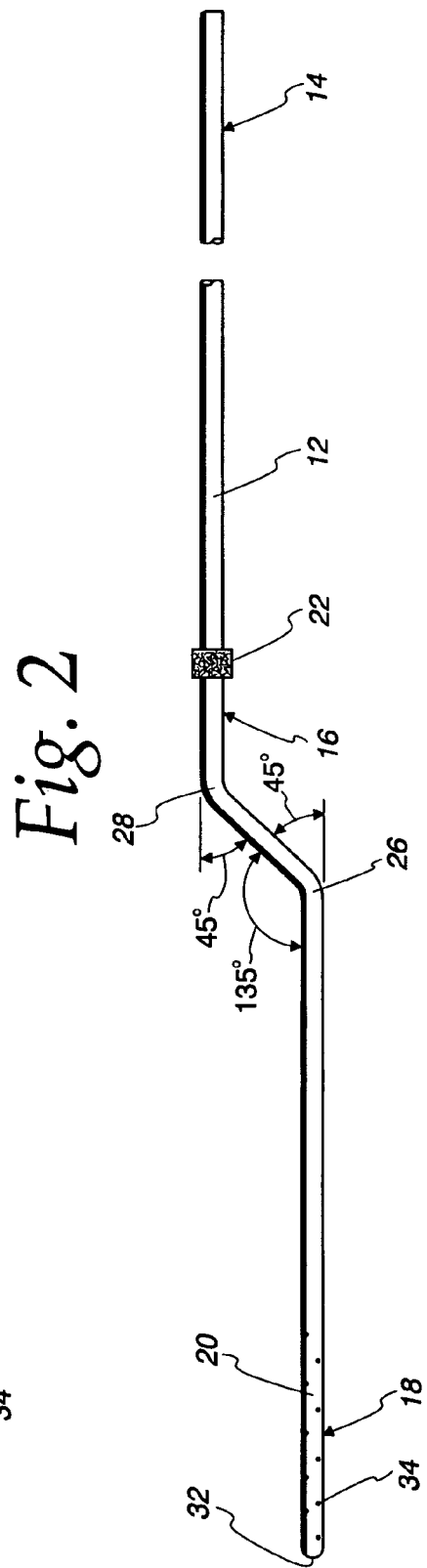

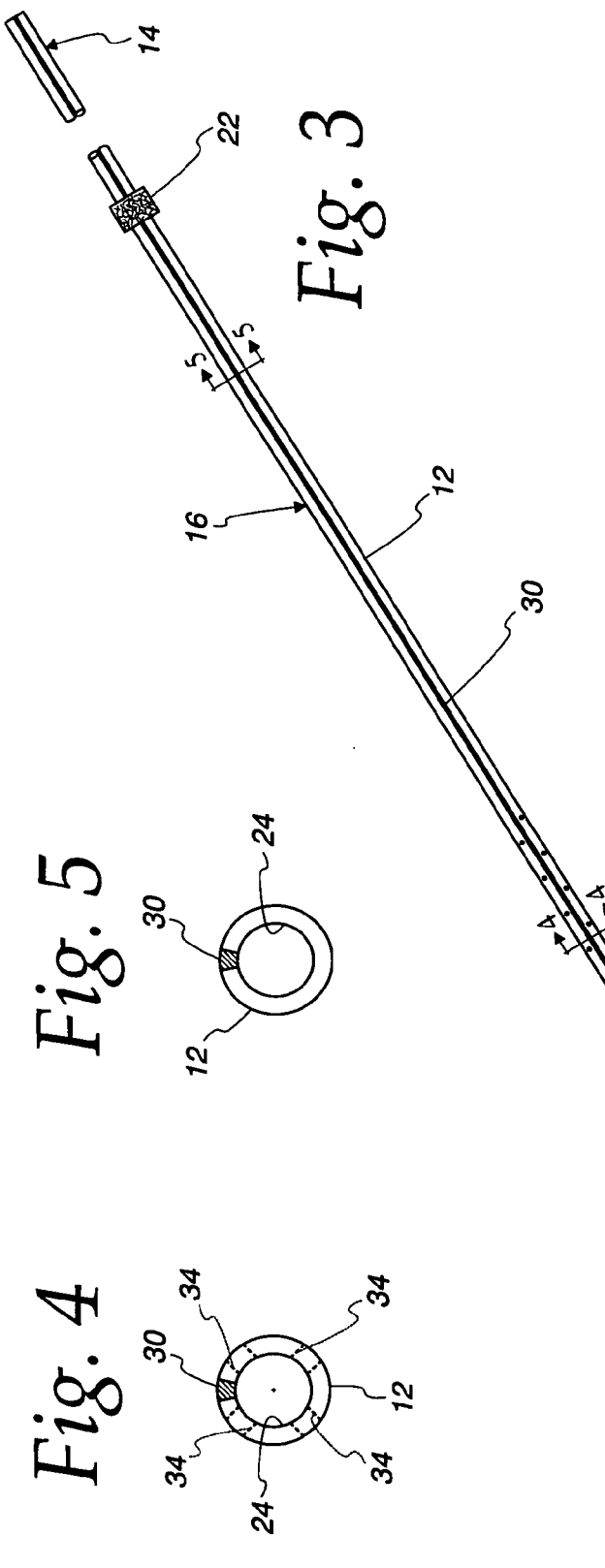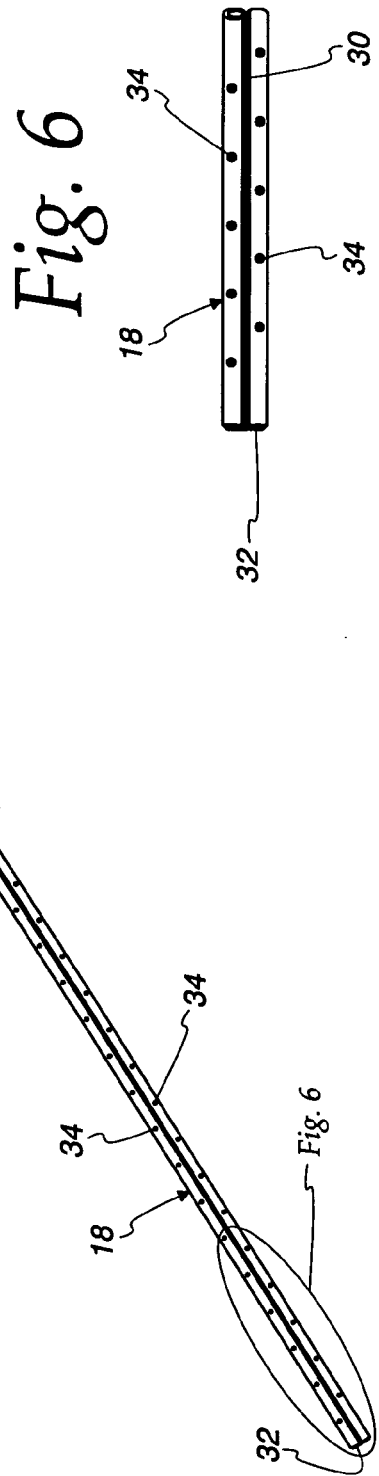

CATHETER

FIELD OF INVENTION

This invention relates generally to catheters suitable for the exchange of fluid, i.e., liquid or gas in a body cavity.

BACKGROUND OF INVENTION

Drainage catheters are utilized for percutaneous removal of accumulated fluids from body cavities such as the peritoneal cavity or the pleural cavity. Such fluids include ascites or pleural fluid that accumulates as a result of malignancies. The accumulated fluids may cause a variety of symptoms such as chest pain, shortness of breath, nausea, non-productive cough, fever, weight loss and the like. While such fluid removal is not curative, per se, it is palliative to the patient and needs to be done repeatedly.

Preferably such palliative drainage can be achieved percutaneously by the placement of a tunneled peritoneal or pleural catheter.

Currently available drainage catheters are straight catheters that, during implantation, often slide up along the pleural wall so that only a few, if any, side drain apertures remain immersed in the pleural fluid. The drainage catheter of the present invention avoids or at least minimizes such shortcomings and provides a catheter that remains properly positioned after implantation and does not apply pressure on the adjacent tissue.

SUMMARY OF INVENTION

A catheter of the present invention is an elongated, flexible tube of uniform diameter that defines a lumen and terminates at its distal portion in a normally spiroidal configuration, preferably as a substantially planar coil. The flexible tube is provided with a subcutaneous cuff on the exterior of the tube.

The spiroidal distal portion is provided with a plurality of spaced drain apertures that provide fluid communication between exterior of the coiled portion of the flexible tube and the lumen. The distal portion, in its normal, spiroidal configuration is substantially centered with respect to the adjacent midportion of the flexible tube.

A midportion of the flexible tube is provided with at least one pair of opposed offsets, each less than 90 degrees, situated in the region between the subcutaneous cuff and the coil. The first offset of the tube preferably is at about 20 degrees to about 75 degrees, more preferably is at about 45 degrees to the plane of the spiroidal distal portion. The second offset is opposite to the first offset and is at about the same angle relative to a plane substantially parallel to but spaced from the plane of the spiroidal distal portion. The sum effect of these two offsets is a relocation of the proximal part of the flexible tube to a new path parallel to the plane of the distal portion of the flexible tube. These two offsets oppose one another, and are spaced from one another about six tube diameters. The second offset is situated about five tube diameters from the subcutaneous cuff.

For implantation, the normally spiroidal distal portion, as well as the two offsets, are temporarily straightened by introducing into the lumen of the flexible tube a stiffening rod and then the resulting, temporarily straightened catheter is introduced via an appropriate incision into the targeted body cavity. For implantation into the pleural cavity, an incision can be made between adjacent ribs of the patient's rib cage in a direction superiorly and posteriorly toward the pleural space. For implantation into the peritoneal cavity, the temporarily straightened catheter is inserted through an incision in the abdominal wall and advanced into the peritoneum.

BRIEF DESCRIPTION OF THE DRAWINGS

In the drawings,

FIG. 1 is a top view of a drainage catheter embodying the present invention;

FIG. 2 is a side elevational view of the drainage catheter shown in FIG. 1;

FIG. 3 is a top view of the drainage catheter, temporarily straightened preparatory to implantation;

FIG. 4 is an enlarged cross-sectional view of the catheter of FIG. 3 taken along plane 4-4;

FIG. 5 is an enlarged cross-sectional view of the catheter of FIG. 3 taken along plane 5-5; and FIG. 6 is an enlarged agmentary view of a temporarily straightened distal portion of a catheter embodying the present invention and illustrating a preferred arrangement of drain apertures.

DESCRIPTION OF PREFERRED EMBODIMENTS

Referring to FIGS. 1 and 2, drainage catheter 10 includes an elongated, flexible tube 12 of substantially uniform diameter which has a proximal portion 14, a midportion 16, and a distal portion 18. Tube 12 defines a lumen 24 (FIGS. 4 and 5).

In its normal configuration, distal portion 18 of catheter 10 is in the form of substantially planar coil 20. For purposes of introduction or implantation into a body cavity of a patient in need of a catheter or fluid drainage, coil 20 can be temporarily straightened as shown in FIG. 3 by inserting into the lumen thereof a relatively stiffer member such as a stylette and the like.

In normal, operational configuration, i.e., after implantation and stylette removal, catheter 10 returns to the shape shown in FIGS. 1 and 2, with coil 20 substantially centered with respect to midportion 16 of tube 12 as shown in FIG. 1. After resuming normal spiroidal configuration, the outer diameter of coil 20 is about 10 to 18 outside diameters of flexible tube 12. The curvature for coil 20 is progressively increasing from the distal end of the coil, i.e., the coil gets progressively larger. Coil 20 also is the distal end portion of flexible tube 12. The radial dimension of the curvature along the coil preferably is in the range of about 5 to about 9 outside diameters of flexible tube 12.

The outside diameter of the flexible tube usually is in the range of about 6.5 millimeters to about 2.5 millimeters, preferably about 5.5 millimeters to about 3.5 millimeters, although the outside diameter can be larger or smaller as deemed appropriate. For an adult drainage catheter, a particularly preferred outside diameter of the flexible tube is about 5 millimeters, and for a pediatric drainage catheter the preferred outside diameter is about 3.7 millimeters.

Likewise, the inside diameter of the flexible tube (i.e., the lumen diameter) usually is in the range of about 5 millimeters to about 1.5 millimeters, preferably about 3.8 millimeters to about 2.3 millimeters, although the inside diameter can be larger or smaller as deemed appropriate. For an adult drainage catheter, the preferred inside diameter is about 3.7 millimeters, and for a pediatric drainage catheter the preferred inside diameter is about 2.5 millimeters.

The flexible tube 12 at midportion 16 thereof has at least one cuff 22 permanently affixed to the exterior of flexible tube 12. The function of cuff 22 is to enable body tissue to grow into the material of the cuff, thereby securing the catheter to the patient after implantation and also thereby to become an effective barrier to external bacteria and potential infection. Typically one cuff, such as cuff 22 shown in FIG. 2 is sufficient; however, more than one cuff can be provided, if desired.

In the region of midportion 16 there is provided a pair of opposed offsets 26 and 28 as best seen in FIG. 2. Offset 26 is defined by flexible tube 12 bent at an angle of about 45 degrees relative to the place of coil 20, and offset 28 is defined by flexible tube 12 bent at an angle of about 45 degrees relative to a plane substantially parallel to but spaced from the plane of coil 20. Stated in another way, at both offsets 26 and 28 flexible tube 12 form an included angle of about 135 degrees. Offset 26 is typically spaced about five tube outside diameters from cuff 22. Offset 26 and offset 28 are commonly spaced from one another about 6 tube outside diameters. It is understood that the dimensions can be altered as deemed appropriate. The dimensions may very from 2 to 8 tube diameters as deemed appropriate. The offset angle is less than 90 degree, preferably about 20 to about 75 degrees more preferably about 45 degrees. If desired, a cuff such as cuff 22 can be situated between the offsets, or such a cuff provided in addition to cuff 22. More than one pair of opposed offsets can be provided, if desired.

A radiopaque stripe 30 extends along the length of tube 20 as shown in FIGS. 3, 4, 5 and 6. Radiopaque stripe 30, usually barium sulfate U.S.P., by nature opaque white, with or without added contrasting colorant, preferably blue, permits monitoring catheter 10 position during and after implantation.

Distal end 32 of catheter 10 is open to permit passage of the fluid to be drained or infused. Distal portion 18 also is provided with an array of spaced apertures 34 for the same purpose. The aperture rows can be offset longitudinally along tube 12 in the coiled portion thereof (FIGS. 1 and 3) as well as radially about the periphery of tube 12 (FIG. 4). The positionings, spacing and distribution of apertures 34 can vary as desired. Usually the apertures have a diameter in the range of about 0.9 to about 1.2 millimeters. A preferred array of apertures 34 is illustrated in FIG. 6 where apertures 34 are arranged into four rows, peripherally spaced and with each row offset relative to an adjacent row, the apertures having a diameter of about 1.1 mm in a flexible tube 12 having an outside diameter of about 5.1 millimeters, spaced longitudinally at about 5 to about 15 mm intervals, preferably about 10 mm intervals, and spaced radially about 90 degrees from one another about the periphery of tube 12 (see FIG. 4).

Flexible tube 12 preferably is made of medical grade silicone tubing, e.g., NuSil-Med 4750/4755. Preferred material of construction for subcutaneous cuff 22 is polyester felt bonded to flexible tube 12 by an appropriate adhesive. In the case of medical grade silicone tubing a preferred silicone adhesive is ethyltriacetoxysilane filled with amorphous silica, and the like, commercially available under the designation Nusil MED-1511 from NuSil Technology, Inc., Carpenteria, Calif., U.S.A.

For pleural fluid drainage, a catheter embodying the present invention is implanted into the pleural cavity. Several surgical pleural catheter implantation techniques can be utilized. However, the most common method is what is called the Modified Seldinger Technique. The original Seldinger technique, is defined as a technique " . . . for percutaneous puncture of arteries or veins, used in angiography." See, for example, Dorland's Illustrated Medical Dictionary, 25$^{th}$ ed., W.B. Saunders Co., Philadelphia, Pa. (1974) p. 1543.

There are a few variations on the Modified Seldinger approach that are suitable for use with this present invention. All versions of this technique are always performed in an aseptic manner in one of several locations, including the operating room (theatre), intensive care unit (ICU), hospital outpatient facility (surgery, laparoscopy, or radiology sites), or a suitably equipped doctor's office. The medical specialists who implant these catheters include thoracic surgeons, interventional radiologists, and interventional pulmonologists.

The patient is admitted to the implantation facility. Pre-operative sedation (conscious sedation) is commonly administered. Blood pressure, oximetry, and cardiac monitoring are commonly performed throughout the implantation procedure. Some specialists monitor only one of the above indicators, and some do not monitor these indicators at all. The skin is prepped in a manner typical of all invasive percutaneous techniques. A localized injection of 1% lidocaine is administered in the midaxiallary line, typically " . . . at 1-2 rib interspaces below the level of dullness to percussion determined during the physical examination." [Rubins J., "Pleural Effusion," Peters et al., eds., Emedicine (2008) accessible online at the website emedicine.com/med/topic1843.htm: article updated 5 Jun. 2008; accessed 12 Aug. 2008.). Site location may also be confirmed by use of radiography, ultrasound, or CT scan. A larger bore needle, typically 18 gauge, is inserted into the pleural space at a " . . . slight posterior angalation." [Pollak J S, et al., J. Vasc. Interv. Radial. 12(2): 201-8 (2001)]. An outflow of pleural fluid confirms successful entry into the pleural cavity. A 0.038-inch braided guide wire is inserted into and through the needle into the pleural cavity. The needle is withdrawn over the wire.

The proximal end of the guide wire is inserted into the distal, narrow end of the expandable Luke™ Guide (3.0 mm dia., 9 Fr), or a standard split sheath with dilator (6.7 mm dia., 20 Fr), and out of the proximal end of the Guide. The Luke™ Guide is inserted into the pleural cavity over the guide wire, following it into the pleural space. The wire is removed, leaving the Guide in place. The Luke™ Guide is secured by clamping the tab of the Guide with a hemostat. The Guide is dilated with the small dilator (4.6 mm; 14 Fr). A larger dilator (6.4 mm; 19 Fr) is used only as necessary, if a lot of resistance is felt while dilating the Guide with the small diameter dilator.

The catheter stylette (stiffening rod) is lubricated with sterile surgical lubricating gel or sterile saline, and inserted into the catheter from the proximal end to the distal end. The stylette temporarily straightens the catheter and also makes it stiff enough to be inserted through the Luke™ Guide into the pleural cavity.

Lubricating gel is applied to the distal end of the catheter. The catheter is inserted into the Guide, with the radiopaque stripe facing upwards (relative to the torso) so that the plan of the coil is correctly oriented in the pleural space. This is true for both left- and right-side placements. When the catheter is inserted, the practitioner must not insert more than 5.0-7.0 cm (2.0-3.0 in) at one time, without retracting the stylette. While holding the stylette stationary, the practitioner then slides the catheter off the stylette and into the pleural cavity, always keeping the radiopaque stripe in the same position.

The physician continues to advance the catheter so that the catheter offset is within the intercostal space (i.e., between the ribs). The stylette is then removed and the cap is temporarily affixed to the end of the catheter to temporarily stop fluid drainage. The catheter is checked and adjusted if necessary to ensure (1) that the radiopaque stripe is in the correct position; and (2) that the catheter offset is within the intercostal space.

The external part of the pleural catheter is tunneled under the patient's skin so that the proposed skin exit-site for the external part of the catheter has a slight downward-facing bend from the implantation site. The catheter is tunneled out through the subcutaneous tissue and out of the skin.

The practitioner continually ensures during the tunneling process that the radiopaque stripe is not twisted, and that the offset part of the catheter is not dislodged from the intercostal space.

After the catheter has been tunneled, a catheter connector, with its one-way valve, is inserted into the distal catheter end. The entire length of the visible catheter segment is inspected to verify correct positioning and to ensure that the catheter is not twisted. The primary incision site is then closed in the typical manner, and dressed appropriately. There is no need for a suture to be placed at the exit-site. Only appropriate dressing and tape is to be used at the exit-site itself to immobilize the catheter and to protect the exit-site.

The sterile lid of the drain/vacuum canister set with its two attached sterile tubes is then attached to the catheter and to the vacuum pump.

When sufficient fluid has been drained off (maximum 1.5 L for pleural fluid; 3.0-5.0 L for ascites fluid), the pump is turned off. The respective tubes are disconnected. The catheter valve end is wiped with isopropyl alcohol, and a sterile protective cap is attached. The catheter is secured to the patient with dressing and tape. The collected fluid, canister, and tubing lines are discarded as per standard aseptic procedures.

The implantation instructions described above are typical for insertion of this catheter into the pleural cavity. The instructions to implant this catheter into the abdominal cavity are similar, and are known to the practitioner.

The major difference is the location of the implantation site. While there are a number of suitable abdominal sites, the most commonly selected site is approximately 3 cm from the patient's midline and approximately 15 cm above the pubic symphysis.

There are a number of techniques which can be used to implant this catheter into the abdominal cavity, including general surgery (cut-down), laparoscopy, and Modified Seldinger Technique. Practitioners are familiar with the details, merits, and weaknesses of each technique, and are to choose the one most suitable for the patient.

Tunneling the catheter is done in the manner described above for tunneling the pleural catheter. The balance of the procedure for the ascites catheter mimics that used for the pleural catheter.

The foregoing description and the drawings are illustrative, and are not to be taken as limiting. Still other variations of the described catheter are possible and will readily present themselves to those skilled in the art.

I claim:

1. A catheter suitable for drainage or infusion of fluids which comprises:
   an elongated, flexible tube of substantially uniform diameter, defining a lumen, and having a proximal portion, a midportion, and a distal portion in a normally spiroidal configuration;
   a subcutaneous cuff permanently affixed to the exterior of the flexible tube and at about the midportion thereof;
   the normally spiroidal distal portion forming a substantially planar coil having a plurality of spaced drain apertures providing fluid communication between exterior of the flexible tube and the lumen, and being substantially centered with respect to the midportion of the flexible tube;
   the flexible tube defining a first offset of less than 90 degrees relative to the plane of the coil and a second offset of less than 90 degrees relative to a plane substantially parallel to but spaced from the plane of the spiroidal distal portion, said first and second offsets being situated at the mid portion of the flexible tube, spaced apart about six tube outside diameters.

2. The drainage or infusion catheter in accordance with claim 1 wherein the outside diameter of the spiroidal configuration is about 10 to 18 outside tube diameters.

3. The drainage or infusion catheter in accordance with claim 1 wherein the spiroidal curvature is progressively increasing from the distal end of the flexible tube.

4. The drainage or infusion catheter in accordance with claim 1 wherein the tube is provided with a radiopaque stripe along the entire length of the tube.

5. The drainage or infusion catheter in accordance with claim 1 wherein the drain apertures are spaced longitudinally along the flexible tube as well as radially about the periphery of the flexible tube and offset from each other.

6. The drainage or infusion catheter in accordance with claim 5 wherein the apertures are spaced at about 5 to about 15 millimeter intervals.

7. The drainage or infusion catheter in accordance with claim 5 wherein the apertures are spaced at about 10 millimeter intervals.

8. The drainage or infusion catheter in accordance with claim 5 wherein the apertures have diameter in the range of about 0.9 to about 1.2 millimeters.

9. The drainage or infusion catheter in accordance with claim 1 wherein the flexible tube has an outside diameter in the range of about 6.5 to about 2.5 millimeters.

10. The drainage or infusion catheter in accordance with claim 1 wherein the flexible tube has an outside diameter in the range of about 5.5 to about 3.5 millimeters.

11. The drainage or infusion catheter in accordance with claim 1 wherein the flexible tube has an inside diameter in the range of about 5 millimeters to about 1.5 millimeters.

12. The drainage or infusion catheter in accordance with claim 1 wherein the flexible tube has an inside diameter in the range of about 3.8 millimeters ro about 2.3 millimeters.

13. A drainage or infusion catheter which comprises:
   an elongated, flexible tube having a substantially uniform outside diameter of about 5 millimeters, defining a lumen having a diameter of about 3.5 millimeters and having a proximal portion, a midportion, and a distal portion which is normally in the form of a substantially planar coil;
   a subcutaneous cuff permanently affixed to the exterior of the flexible tube and at about the midportion thereof;
   the coil having a plurality of spaced drain apertures providing fluid or gas communication between exterior of the flexible tube and the lumen, and being substantially centered with respect to the midportion of the flexible tube;
   the flexible tube defining a first offset of about 45 degrees relative to the plane of the coil and a second, opposite offset of about 45 degrees relative to a plane substantially parallel to but spaced from the plane of the coil, said first and second offsets being situated between said subcutaneous cuff and the proximal end of the flexible tube, spaced apart about six tube outside diameters, and the second offset being situated about five tube outside diameters from said subcutaneous cuff.

14. The drainage or infusion catheter in accordance with claim 13 wherein the coil outside diameter is about 10 to about 18 tube outside diameters.

15. The drainage or infusion catheter in accordance with claim 13 wherein the curvature of the coil is progressively decreasing from the distal end of the coil.

16. The drainage or infusion catheter in accordance with claim 13 wherein the tube is provided with a radiopaque stripe along the entire length of the tube.

17. The drainage or infusion catheter in accordance with claim 13 wherein the drain apertures are spaced longitudinally along the flexible tube as well as radially about the periphery of the flexible tube and offset from one another.

18. The drainage or infusion catheter in accordance with claim 17 wherein the apertures are spaced at about 5 to about 15 millimeter intervals.

19. The drainage or infusion catheter in accordance with claim 1 wherein the apertures have diameter in the range of about 0.9 to about 1.2 millimeters.

* * * * *